(12) United States Patent
Mark et al.

(10) Patent No.: US 6,419,641 B1
(45) Date of Patent: Jul. 16, 2002

(54) FLEXIBLE TIP MEDICAL INSTRUMENT

(75) Inventors: Joseph L. Mark, Indianapolis; Michael E. Miller, Trafalgar, both of IN (US)

(73) Assignee: Promex, LLC, Franklin, IN (US)

( * ) Notice: Subject to any disclaimer, the term of this patent is extended or adjusted under 35 U.S.C. 154(b) by 15 days.

(21) Appl. No.: 09/723,845

(22) Filed: Nov. 28, 2000

(51) Int. Cl.$^7$ ............................................. A61B 10/00
(52) U.S. Cl. ........................ 600/564; 600/567; 606/167; 604/164.01
(58) Field of Search .......................... 600/562, 564–567; 606/79, 159, 167, 170, 181; 604/22, 164.01, 164.11, 523

(56) References Cited

U.S. PATENT DOCUMENTS

| | | | | |
|---|---|---|---|---|
| 4,246,902 A | * | 1/1981 | Martinez | 604/22 |
| 4,650,472 A | | 3/1987 | Bates | 604/158 |
| 4,907,598 A | | 3/1990 | Bauer | 600/566 |
| 5,106,364 A | * | 4/1992 | Hayafuli et al. | 604/22 |
| 5,273,051 A | | 12/1993 | Wilk | 600/564 |
| 5,370,651 A | | 12/1994 | Summers | 606/159 |
| 5,431,673 A | | 7/1995 | Summers et al. | 606/170 |
| 5,458,112 A | | 10/1995 | Weaver | 600/566 |
| 5,620,415 A | | 4/1997 | Lucey et al. | 604/22 |
| 5,620,447 A | | 4/1997 | Smith et al. | 606/79 |
| 5,669,926 A | * | 9/1997 | Aust et al. | 606/170 |
| 5,700,253 A | | 12/1997 | Parker | 604/526 |
| 5,741,261 A | | 4/1998 | Moskovitz et al. | 606/79 |
| 5,755,731 A | | 5/1998 | Grinberg | 606/170 |
| 5,797,907 A | * | 8/1998 | Clement | 606/49 |
| 5,800,389 A | | 9/1998 | Burney et al. | 604/164.01 |
| 5,851,212 A | * | 12/1998 | Zirps et al. | 606/167 |
| 5,911,701 A | | 6/1999 | Miller et al. | 604/22 |
| 5,989,196 A | * | 11/1999 | Chu et al. | 600/567 |
| 5,997,560 A | * | 12/1999 | Miller | 606/170 |
| 6,012,494 A | | 1/2000 | Balazs | 138/119 |
| 6,019,743 A | | 2/2000 | Cole et al. | 604/15 |
| 6,048,339 A | | 4/2000 | Zirps et al. | 604/525 |
| 6,056,700 A | | 5/2000 | Burney et al. | 600/564 |
| 6,251,120 B1 | * | 6/2001 | Dorn | 606/170 |
| 6,296,624 B1 | * | 10/2001 | Gerber et al. | 604/164.11 |

OTHER PUBLICATIONS

Brochure for Intratherapeutics, Inc., "A Vision for the Future".
Web page www.mirs.org/rounds/ir_tjilbfrm.htm, "Transjugular Liver Biopsy" written by David H. Riggans et al. Jul. 11, 1999.
Brochure by Smith & Nephew Dyonics, Inc., "Extend your anthroscopic reach", 1999.

* cited by examiner

*Primary Examiner*—Kevin Shaver
*Assistant Examiner*—Charles Marmor, II
(74) *Attorney, Agent, or Firm*—Leagre Chandler & Millard LLP

(57) ABSTRACT

A biopsy device includes a flexible distal portion for obtaining a biopsy sample from a biopsy site. The device includes a coring cannula with a wall defined between a proximal end and a distal end and defining a lumen therebetween. The wall of the cannula defines a coring relief notch adjacent the distal end that has a length along a longitudinal axis of the cannula longer than a diameter of the coring cannula. A wire is slidably disposable within the lumen of the coring cannula and has a proximal end and a distal end and defines a sampling cavity adjacent the distal end. A wire relief notch is positioned adjacent the sampling cavity. The wire relief notch has a length along a longitudinal axis of the wire longer than a width of the wire relief notch. A firing mechanism is engaged to the proximal ends of the coring cannula and the wire and the firing mechanism is operable to move the coring cannula relative to the wire from a second position to a first position to trap tissue from the biopsy site in the sampling cavity. The wire is slidable relative to the coring cannula between the first position retracted within the lumen so that the coring cannula covers the sampling cavity and a second position wherein the distal end of the wire is extended away from the coring cannula to expose the cavity to tissue in the biopsy site.

15 Claims, 10 Drawing Sheets

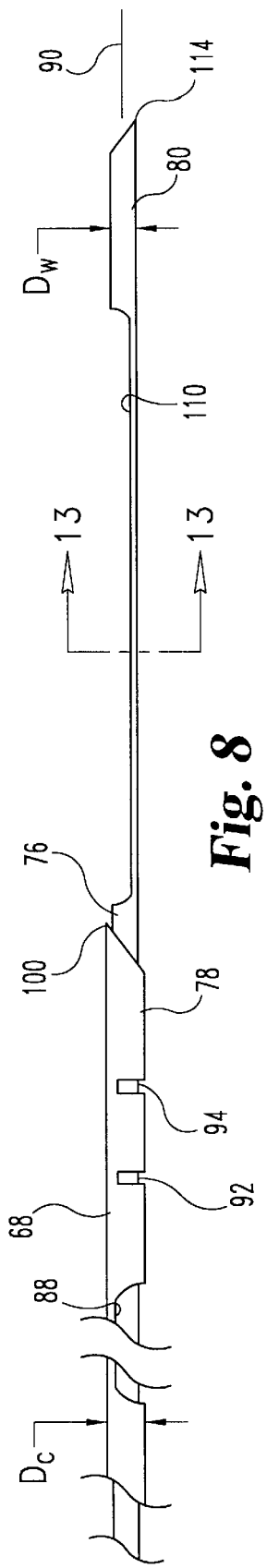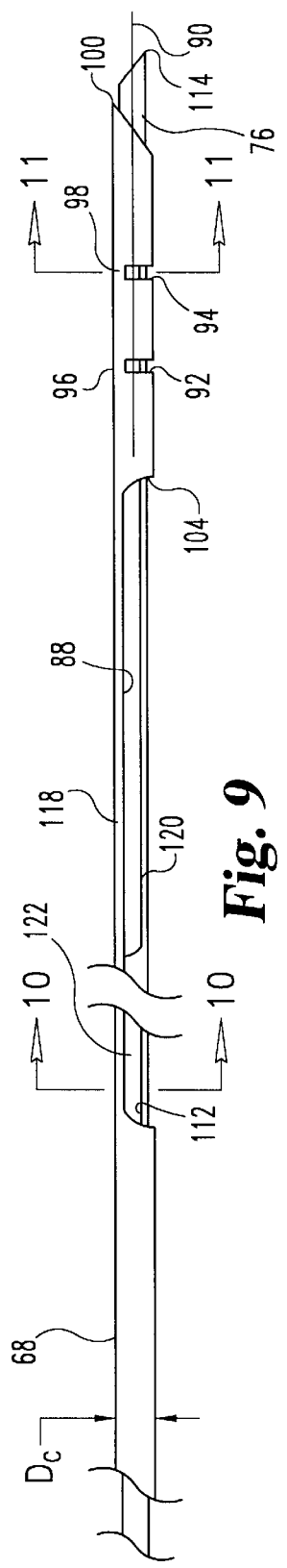
Fig. 8
Fig. 9

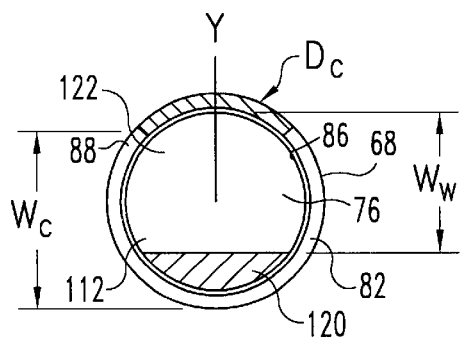
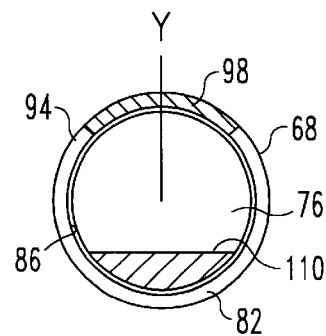
Fig. 10     Fig. 11
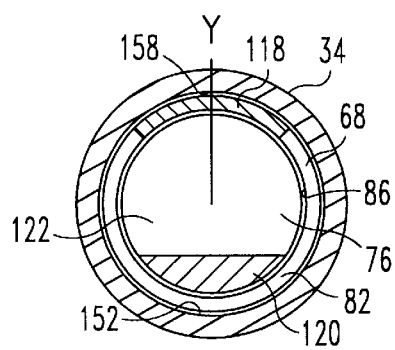
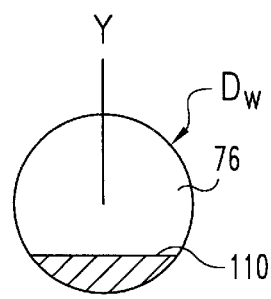
Fig. 12     Fig. 13

FLEXIBLE TIP MEDICAL INSTRUMENT

FIELD OF THE INVENTION

The present invention relates generally to biopsy systems. Specifically, the invention concerns devices for obtaining biopsy samples through veins and arteries.

BACKGROUND OF THE INVENTION

In the practice of diagnostic medicine, it is often necessary or desirable to perform a biopsy, or to sample selected tissue from a living patient for medical evaluation. Cytological and histological studies of the biopsy sample can then be performed as an aid to the diagnosis and treatment of disease. Biopsies can be useful in diagnosing and treating various forms of cancer, as well as other diseases in which a localized area of affected tissue can be identified.

During the biopsy procedure, care is taken to minimize the physical trauma inflicted upon the intervening tissues that surround the affected area or target tissue and at the same time to protect the practitioner from health hazards. One typical biopsy procedure includes inserting a hollow biopsy needle through the intervening tissue into the target tissue to be sampled. The sample tissue is then harvested through the needle by applying suction through the needle, typically with a syringe.

Special considerations apply if the biopsy is to be performed on an internal organ deep within the body such as the liver. Previously, obtaining a tissue sample from an internal organ, such as the liver, was carried out percutaneously by entering the skin in the vicinity of the organ and thereafter extracting a core of liver material through the biopsy needle. This method, although effective in obtaining an adequate amount of tissue from the liver, is no longer acceptable practice, since it is not uncommon for the patient to suffer from serious health complications caused by the biopsy. For example, patients generally experience extreme pain, and additionally, the liver profusely bleeds after percutaneous biopsy. Moreover, liver biopsies are typically performed on patients having liver disease, liver transplants and coagulation disorders, and such conditions further complicate percutaneous liver biopsies.

Alternatively, tissue samples may be obtained without the problems associated with percutaneous biopsy by accessing the liver via a transjugular procedure. Known techniques involve accessing the liver through the jugular vein with an elongated biopsy device. Typically, these biopsy devices are identical to typical single and double action biopsy devices except that the inner and outer needles are elongated to access the liver from the jugular vein.

An example of a typical transjugular single action biopsy device 20 is shown in FIGS. 1–3. Biopsy device 20 includes an outer hollow needle 22 defining a lumen 24 therethrough. An inner needle 26 is slidingly engaged inside lumen 24 and is moveable relative to outer needle 22. The inner needle 26 defines a first or distal end 28 having a tissue cutting point 30 and a cavity 32 adjacent first end 28 for receiving tissue samples. The inner needle 26 is slidable relative to outer needle 22 between a first retracted position (FIG. 3) and a second extended position (FIG. 2). In the first retracted position, inner needle 26 is retracted within lumen 22 so that outer needle 22 covers cavity 32 so that the distal end can be inserted into the liver. In the second extended position, the first end 28 of inner needle 26 is extended away from outer needle 22 to expose cavity 32 to tissues at the biopsy site. Such means are known in the art and commercially available. For example, biopsy devices of this type are available form U.S. Biopsy, Inc., a division of Promex, Inc., 3049 Hudson Street, Franklin, Ind., (317) 736-0128.

During a transjugular liver biopsy an elongated introducer 34, as illustrated in FIG. 4, is inserted through a small incision or puncture made in the skin. The introducer 34 is an elongated, small diameter cannula defining a lumen 36 that receives and guides the distal end 35 of biopsy device 20 to the biopsy site. A tip 38 of the introducer 34 is carefully advanced through venous passageways with the assistance of X-ray or fluoroscopy. Great care is taken to position the tip 38 at the precise location of the intended biopsy site. The biopsy device 20 is then advanced through the introducer lumen 36 and thereafter tissue cutting point 30 of inner needle 26 enters the liver tissue. During this insertion stage of the procedure, inner needle 26 is positioned within outer needle 22 in the first, retracted position (FIG. 3).

Once device 20 has been positioned at the targeted site for the biopsy, inner needle 26 is momentarily driven into liver tissue far enough to expose cavity 32 of inner needle 26. Liver tissue then prolapses into cavity 32. The device is then fired to advance outer needle 22 along inner needle 26 to cover cavity 32. This forward movement of outer needle 22 severs the prolapsed tissue to obtain a tissue sample, which becomes trapped in cavity 32 of inner needle 26. Movement of inner and outer needles 26, 22 to capture a sample occur almost instantaneously via firing mechanism 27 engaged with proximal ends 29 of needles 26, 22. The quality of the sample is largely dependent on the thrust or "strike" of outer needle 22 securing the tissue since the tissue is often parenchymatous tissue and is gelatinous in consistency. With outer needle 22 blocking the opening of cavity 32, biopsy assembly 20 may then be withdrawn, carefully backing out of introducer 34 leaving the introducer in place. Biopsy device 20 is then withdrawn from the target site carrying the sample within cavity 32. To collect the biopsy sample outer needle 22 is once again retracted to expose cavity 32 of inner needle 26. Typically, the biopsy device is re-inserted into the introducer to collect another biopsy sample. The procedure may be repeated several more times until satisfactory samples have been obtained.

A problem associated with this type of biopsy device is that the rigid inner and outer needles 26, 22 are metallic, commonly stainless steel, and lack the flexibility to freely move within the introducer 34 due to the significant curve 42 located at the introducer's distal end 44 (FIG. 4). The curve 42 of the introducer 34 causes the inner and outer needle 26, 22 to bind with an inner wall 46 comprising lumen 36 of the introducer 34, which in turn, can cause movement of the introducer. Consequently, the introducer is prone to movement due to the formation of resistance between inner and outer needles 26, 22 traversing curve 42 in introducer 34. Movement of the introducer once it is ideally placed is undesirable since damage to the surrounding tissue and poor biopsy samples are frequently the result of such movement. Moreover, since the curve 42 in the introducer causes continuous binding, even after the outer needle 22 has cleared the curve 42, much of the momentum imparted on inner and outer needles 26, 22 via spring force of firing mechanism 27 is utilized to overcome this binding or frictional force. Consequently, the effectiveness of the firing mechanism 27 is diminished resulting in recovery of small and fractured tissue specimens. Moreover, repeatedly firing the biopsy device 20 during subsequent sampling events causes the sliding surfaces of the outer needle 22 and inner wall 46 of introducer 34 to become "galled" i.e., deformation of the sliding surfaces, resulting in an additional and significant decrease in performance of the firing mechanism 27. As a result, little if any tissue is recovered and the device 20 may be permanently damaged before an adequate specimen is captured. The damaged device is then discarded and additional devices must then be used to capture adequate and sufficient tissue. This is unfortunately common and leads to a significant and unwarranted cost increase due to equipment, personnel and room charges, as well as an extended biopsy procedure for the patient.

Biopsy of an organ deep within the body, such as the liver, requires the introducer tip to be implanted a significant depth. Since the quality of the specimen is largely dependent on the striking momentum of the biopsy device over this long distance, a large degree of stiffness of the needles is necessary to transmit striking force from the firing device to the tip of the coring needles. Unfortunately, the needles tend to bind with the lumen walls of the long introducer at the bend. Thus, what is needed is a needle assembly that provides flexibility without compromising the stiffness and integrity of the needles.

U.S. Pat. No. 4,907,598 to Bauer discloses an alternative to rigid inner and outer needle assemblies by employing a flexible cannula and wire assembly that flexes as the curve in the introducer is traversed. The wire, comprised of a cable, and the cannula, provided with a stacked coil arrangement are designed to enhance flexibility. Problematically, the flexible cable and cannula assembly are generally flaccid in disposition providing a biopsy tip, located at the distal end of the cable and cannula assembly, that is unwieldily and uncontrollable. Moreover, a significant amount of energy of the firing device is lost by the flexible cannula and wire assembly as it yields when the firing device is activated. Consequently, small and fragmented specimens are captured and multiple additional firings are generally required.

U.S. Pat. No. 5,620,415 to Lucey et al. discloses a surgical device constructed to transmit forces applied at a handpiece through a bend region of a rigid outer tube. Force is transmitted from the handpiece to a cutting tool through a pair of internested tubes supported within the rigid tube. The assembly provides a flexible region caused by the inner tube having a series of circumferential slots that lie completely within the bend region at the time the handpiece is operated. In addition, the circumferential slots are parallel to each other and extend from opposite sides of the inner tube to form an accordion-like design. These circumferential slots provide a limited measure of binding relief at the bend, however an unsatisfactory level of relief for deep internal organ biopsy. In addition, these slots result in a loss of axial strength, and ultimately, a loss in precision between the stationary tube and the inner movable tube. As an added disadvantage, it is very expensive to produce the accordion-like design of these slots.

U.S. Pat. No. 5,911,701 to Miller and Ireland discloses a surgical cutting instrument having a curved outer cannula which slidably supports a cutting member disposed therein. The cutting member is attached to a continuous tubular member consisting of a rigid portion affixed to a flexible body portion extending along the curve of the outer cannula. To ensure a propitious measure of axial rigidity in the flexible body portion a plurality of driving cables are provided within the flexible body portion. Although the device is flexible, it is a motorized surgical cutting device, and the degree of complexity introduced by the concept is not desirable in the single and double action biopsy devices used for intravascular accessed biopsy procedures.

A need has remained for a transjugular biopsy device that overcomes the resultant binding force imparted by the introducer on the needle coring assembly. Additionally, what is needed is a transjugular biopsy device amenable to repeated uses without a measurable degradation in performance. Further, an inexpensive biopsy device that may be repeatedly fired without damage to the device would be desirable.

SUMMARY OF THE INVENTION

Accordingly, the present invention overcomes the disadvantages of prior biopsy devices by providing a biopsy device having a flexible distal portion for obtaining a biopsy sample from a biopsy site. The devices include a coring cannula having a wall between a proximal end and a distal end and defining a lumen therebetween. A wire is slidably disposable within the lumen of the coring cannula and defines a sampling cavity adjacent the distal end and a wire relief notch adjacent the sampling cavity. A firing mechanism is engaged to the proximal ends of the coring cannula and the wire. The firing mechanism is operable to move the coring cannula relative to the wire from the second position to the first position to trap tissue from the biopsy site in the sampling cavity. The wire is slidable relative to the coring cannula between a first position retracted within the lumen so that the coring cannula covers the sampling cavity and a second position wherein the distal end of the wire is extended away from the coring cannula to expose the cavity to tissue in the biopsy site. The wall defines a coring relief notch adjacent the distal end and has a length along a longitudinal axis of the cannula longer than a diameter of the coring cannula. The wire relief notch has a length along a longitudinal axis of the wire longer than a diameter of the wire.

Another aspect of the invention provides a biopsy assembly including an introducer having an elongated cannula defining an introducer lumen between a proximal end and a distal end. The cannula has a curved portion adjacent the distal end. A body portion is attached to the proximal end of the cannula and defines a channel in communication with the introducer lumen. An access port is defined in the body portion in communication with the channel. A biopsy device of this invention is disposable within the introducer lumen through the access port. The distal end of the biopsy device is extendable out through the distal end of the introducer cannula to access tissue.

One object of the invention is to provide biopsy devices and assemblies specifically designed for accessing and performing a biopsy on an internal organ situated deep within a body. One advantage of the present invention is that it can be achieved through inexpensive modifications of existing devices. Yet another advantage of the present invention is its capability to yield a sufficient amount of biopsy samples using a single device. Yet another advantage is that the present invention does not require complicated cabling or the attachment or welding of similar or dissimilar materials to comprise the flexible portions. These and other objects, advantages and features are accomplished according to the devices, assemblies and methods of the present invention.

DESCRIPTION OF THE FIGURES

FIG. 8 is an enlarged plan view of the biopsy device of FIG. 7 depicting the distal end of the biopsy device in a position wherein the coring cannula is retracted (pre firing);

FIG. 9 is an enlarged plan view of the biopsy device of FIG. 7 depicting the distal end of the biopsy device in a position wherein the coring cannula is extended (post firing);

FIG. 10 is a sectional view of the biopsy device of FIG. 9 taken along line 10—10, depicting the wire relief notch and the coring relief notch;

FIG. 11 is a sectional view of the biopsy device of FIG. 9 taken along line 11—11, depicting one of the discrete slots and the sampling cavity;

FIG. 12 is a sectional view of the biopsy assembly of FIG. 16 taken along line 12—12, depicting the wire relief notch interacting with the coring relief notch within the curve of the introducer;

FIG. 13 is a sectional view of the biopsy device of FIG. 8 taken along line 13—13, depicting the sampling cavity;

FIG. 16 is an enlarged fragmentary view of the distal end of the biopsy assembly of FIG. 5, partially in section, illustrating the cannula and wire flexing at the bend of the introducer;

FIG. 17 is an enlarged fragmentary view of the tip of a biopsy device according to the present invention showing an alternative wire tip configuration;

Figure 1:
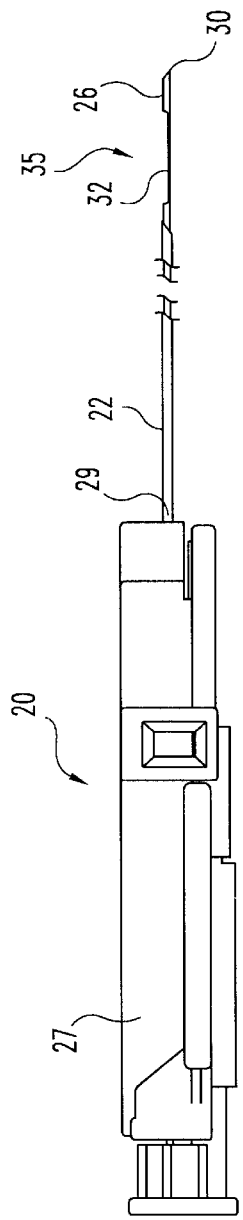
FIG. 1 is plan view of a prior art biopsy device.

Corresponding reference characters indicate corresponding parts throughout the several views. Although the drawings represent an embodiment of the present invention, the drawings are not necessarily to scale and certain features may be exaggerated in order to better illustrate and explain the present invention. The exemplification set out herein illustrates an embodiment of the invention, in one form, and such exemplifications are not to be construed as limiting the scope of the invention in any manner.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention that would normally occur to one skilled in the art to which the invention relates.

The present invention provides devices and assemblies to access an internal organ through a patient's venous and arterial system to obtain a tissue specimen from the target organ. A long narrow tube or introducer cannula is precisely placed through interconnecting veins and arteries along a tortuous path. Previously used coring needle assemblies exhibited pronounced binding with the introducer cannula as the curves of the introducer were traversed. To overcome this binding, the present invention provides a needle coring assembly including a flexible tip having precisely placed relief notches and relief slots disposed in the coring wire and the coring cannula. Although features of the present invention allow the coring needle assembly to flex as it confronts curves in the introducer, the strength, durability and function of the assembly are not compromised.

Figure 4:
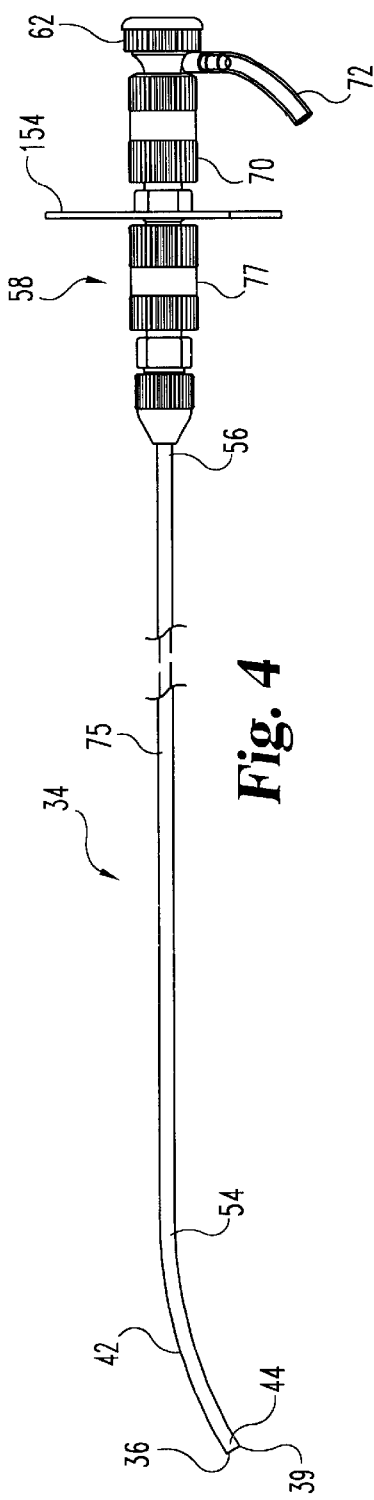
FIG. 4 is a plan view of the introducer of the biopsy assembly of FIG. 5.
Figure 5:
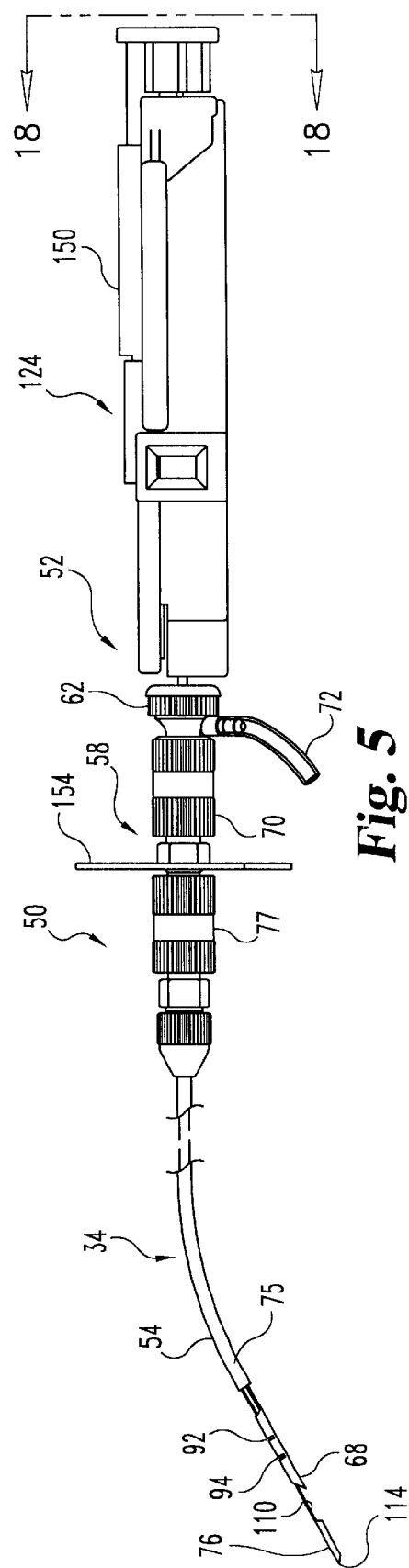
FIG. 5 is a plan view of a first embodiment biopsy assembly according to present invention.
Figure 6:
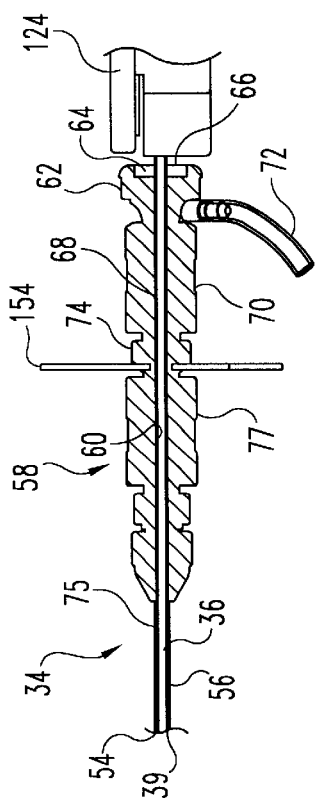
FIG. 6 is an enlarged fragmentary view of the biopsy assembly of FIG. 5, showing the body portion of the introducer in section.

A biopsy assembly 50 according to one embodiment of this invention is shown in FIG. 5. The assembly 50 includes an introducer 34 and a biopsy device 52. The preferred introducers of this invention are available from Cook, Inc. of Bloomington, Ind. FIGS. 4 and 6 illustrate introducer 34, which is provided with an elongated cannula 54 defining an introducer lumen 36 between a proximal end 56 and a distal end 44. Lumen 36 terminates at an opening 39 defined in distal end 44. In this embodiment, cannula 54 has a curved portion 42 adjacent the distal end 44 to navigate the sharp angle at the union of the vena cava and hepatic veins. In other embodiments, the cannula 54 may have other curved portions or be flexible to accommodate the tortuous path along the venous system to an organ of the body. The biopsy devices of this invention will then have flexible regions that correspond to such other curved or flexible portions of the cannula. The cannula 54 is preferably about 60 cm long and includes an inside diameter slightly larger than biopsy device advanced into lumen 36.

Introducer 34 further includes a body portion 58 attached to the proximal end 56 of the cannula 54. Body portion 58 defines a channel 60 in communication with the introducer lumen 36. The body portion 58 includes an access port 66 for the insertion of coring cannula 68 within the body portion 58 which is in communication with the channel 60. The access port includes a connector valve 62 for sealingly receiving a biopsy needle. In a preferred embodiment, valve 62 includes a silicone disk 64 for preventing the backflow of fluids passing along the biopsy device 52 at the site of the disk 64. In a specific embodiment, body portion also includes connector 70 to which polyvinyl tube 72 and Luer lock connector 74 are connected for introducing and aspirating fluids through introducer 34 as is required. Introducer 34 further includes sheath 75 snugly engaged to the exterior of the entire length of cannula 54 and attached to a proximal end 56 thereof through an additional Luer lock 77. Sheath 75 is constructed from a low friction material such as a PTFE or a Nylon composite, so designated, to protect the intima as introducer 34 is advanced through the veins and arteries.

Assembly 50 further includes biopsy device 52, which is disposable within the introducer lumen 36 through the access port 66. One first embodiment of a biopsy device 52 is shown in FIGS. 7–13 and includes coring cannula 68 and a wire 76, which are both flexible at their distal ends 78, 80 for traversing the curved portion 42 in introducer 34 as the biopsy device 52 is inserted into the introducer lumen 36. Wire 76 is preferably a solid, non-cannulated wire. In embodiments in which the introducer is flexible or has a curved portion in another or additional locations, the biopsy devices of this invention will have flexible portions that correspond to the curved or flexible portions of the introducer.

Figure 7:
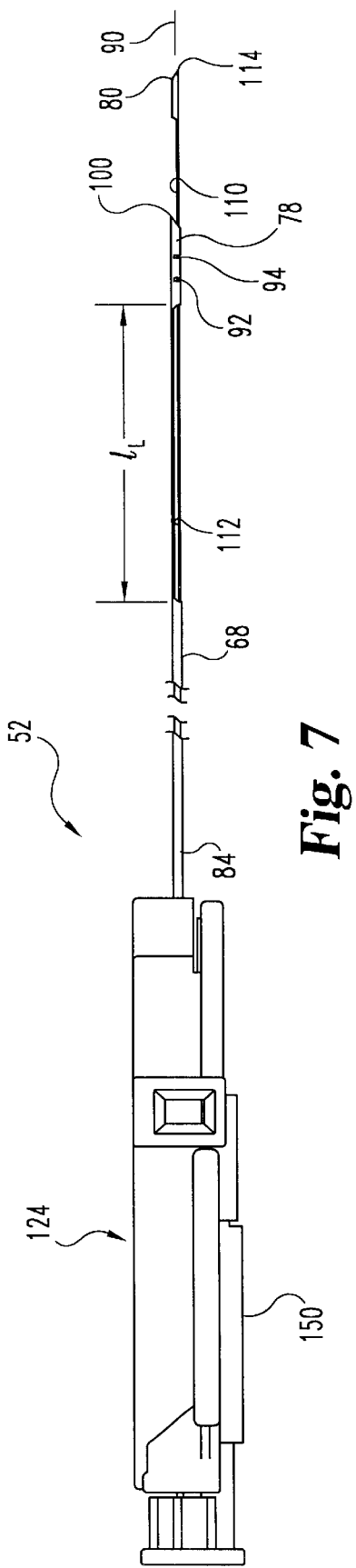
FIG. 7 is a plan view of the biopsy assembly of FIG. 5 showing the introducer removed.

Coring cannula 68 includes a wall 82 (FIG. 10) between a proximal end 84 and a distal end 78 and defines a lumen 86 therebetween. The wall 82 defines an elongated coring relief notch 88 adjacent the distal end 78. As best shown in FIG. 7, the coring relief notch 88 extends along a longitudinal axis 90 of the cannula 68. The length lc of the coring relief notch 88 is longer than the width Wc (FIG. 10) of notch 88. In one specific embodiment, length lc is about 2.0", for example. In the exemplary embodiment, coring cannula 68 is made of stainless steel tubing from between 16 to 20 gage, for example.

Figure 14:
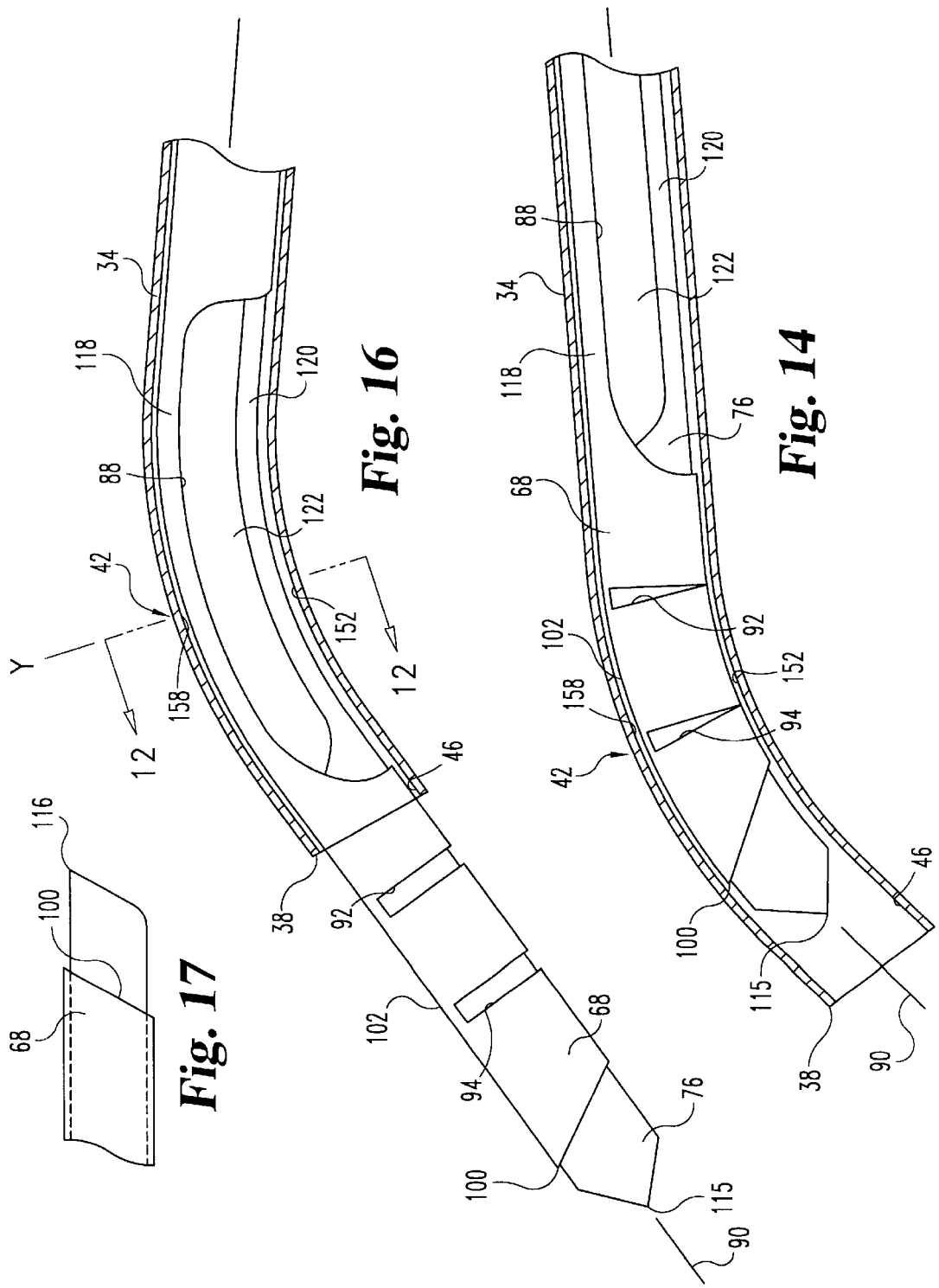
FIG. 14 is an enlarged fragmentary view of the distal end of the biopsy assembly of FIG. 5, partially in section, illustrating the cannula flexing at the bend of the introducer.

Distal end 78 of coring cannula 68, the details of which are best shown in FIGS. 8–9 and 14–16, includes a pair of discrete slots 92 and 94. Each slot 92, 94 extends radially into wall 82 of cannula 68 and flexing portions 96, 98, are adjacently positioned relative to slots 92, 94. In one specific embodiment, discrete slots 92, 94 extend radially a distance of three-fourths the outer diameter $D_c$ of the coring cannula 68 and have respective widths of 0.020", for example. Referring now to FIGS. 11 and 14, as tip 100 of coring cannula 68 traverses curve 42 in introducer 34, each discrete slot 92, 94 allows cannula 68 to temporarily flex reducing sliding resistance between outer surface 102 of cannula 68 and inside surface 46 of introducer 34. Further, flexing portions 96, 98 are sized to allow flexibility in coring cannula 68 yet are structured and arranged to prevent permanent deformation of the flexing portions. In this specific embodiment, the coring cannula defines two discrete slots. However, any number of slots is contemplated depending on the degree and locations where flexibility is required.

Coring relief notch 88 extends partially through wall 82 of coring cannula 68. In contrast to radially formed discrete slots 92, 94 in coring cannula 68, notch 88 extends along longitudinal axis 90 of coring cannula 68 a substantial distance, such as 2.0", as in one specific embodiment for example. Coring relief notch 88 may measure a depth of three fourths of the outer diameter $D_c$ of cannula 68, for example. Referring to FIG. 9, a first end 104 of notch 88 is positioned approximately 0.60" from furthest extent of tip 100 in one specific embodiment. Biopsy device 52 includes wire 76 slidably disposable within the lumen 86 of the coring cannula 68 and is provided with a proximal end 108 and distal end 80. A sampling cavity 110 positioned adjacent the distal end 80. Wire 76 further defines a wire relief notch 112, which is adjacent the sampling cavity 110 in this embodiment. Wire relief notch 112 extends along a longitudinal axis of the wire that is coincident with the longitudinal axis 90 of the cannula 68. The length lw (FIG. 15) of notch 112 is longer than the width Ww (FIG. 10) of notch 112. In one specific embodiment, lw is about 2.0", for example. As best seen in FIGS. 14 and 16, in this particular embodiment wire 76 includes a trocar tip 115 which is angled to a point as is customary to expediently puncture the liver with little or no resistance from the liver tissue. As an alternative to tip 115, tip 116 as illustrated in FIG. 17, includes an angled tip 116, the angle closely tracking the angle of cannula tip 100, to reduce the risk of tip 116 binding with introducer 34 as it traverses curve 42. Yet another alternative to tips 115 and 116 is tip 114, as best illustrated in FIG. 9. Tip 114 of wire 76 is angled opposite to that of tip 100 of cannula 68.

Figure 2:
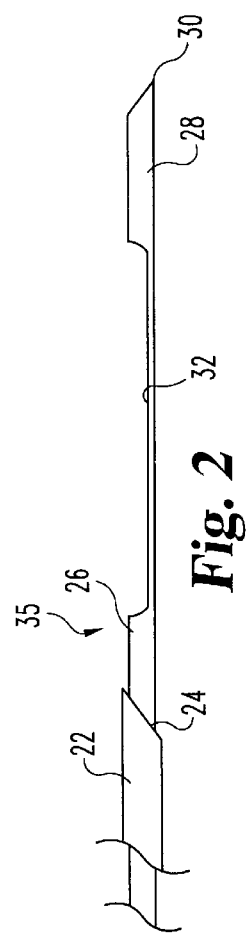
FIG. 2 is an enlarged fragmentary view of FIG. 1 showing detail of the tip with the device in an extended position.
Figure 3:
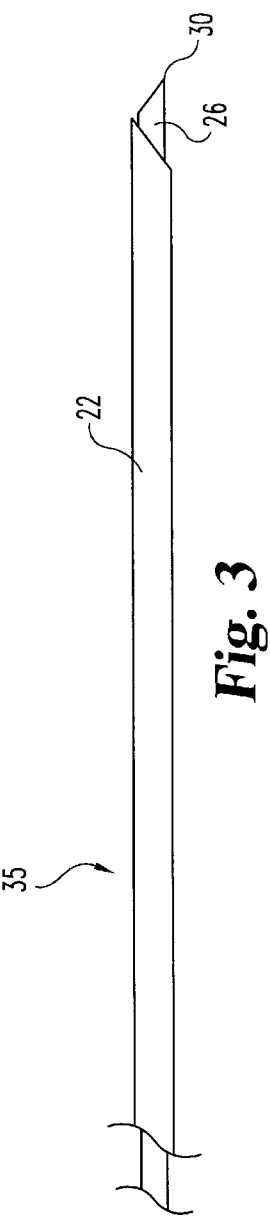
FIG. 3 is an enlarged fragmentary view of FIG. 1 showing detail of the tip with the device in a retracted position.

Referring now to FIGS. 9 and 10, coring relief notch 88 in coring cannula 68 substantially superposes wire relief notch 112 in wire 76 to provide a substantial degree of flexibility to both cannula 68 and wire 76 at the site of curve 42. FIGS. 14 and 16 detail the progression of distal end 78 of coring cannula 68 traversing curve 42 in introducer 34 (FIG. 14), followed by flexible wall portions 118, 120 of coring cannula 68 and wire 76, respectively, traversing curve 42 in introducer 34 (FIG. 16). In contrast to the prior art coring cannula 22 (outer needle) and wire 26 (inner needle), shown in FIGS. 1 and 2, a gap 122 is provided between coring cannula 68 and wire 76 to allow coring cannula 68 and wire 76 to flex as curve 42 is traversed. This flexibility significantly reduces binding between cannula 68 and wire 76. Since gap 122 extends a significant distance along the length of coring cannula 68 and wire 76 at the site of curve 42, cannula 68 and wire 76 remain flexible over the entire throw of the firing device 124. As a consequence, the energy utilized by firing device 124 to advance coring cannula 68 is not adversely affected since there is little or no increase in resistance between coring cannula 68 and wire 76 due to the curve 42.

It is envisioned that as little as one relief or as many as several reliefs may be provided in the cannula such that a significant reduction of resistance is experienced as the cannula 68 traverses curve 42 in introducer 34. However, providing an over abundance of reliefs is preferably avoided since stiffness of the cannula and stylet assembly may be compromised. It is further envisioned that multiple reliefs may be placed at varying positions along the cannula to facilitate reduced resistance between the cannula and an introducer having multiple bends along its length.

FIGS. 10 and 11 detail the relationship between coring relief notch 90 and discrete slot 94. Coring relief notch 88 of cannula 68 is arranged substantially symmetrical respective of reference axis Y. Axis Y corresponds to a zero degree reference and it may be seen that cannula wall 82 is provided between approximately −45 and 45 degrees relative to the Y axis (FIG. 10). Similarly, discrete slot 94 (FIG. 11) is symmetrical relative to reference axis Y and therefore coring relief notch 88 and discrete slot 94 are axially aligned. In other words, coring relief notch 88 and discrete slot 94 are circumferentially aligned relative to one another. In the preferred embodiment, discrete slot 92 is provided with a substantially identical structure and orientation as discrete slot 94.

FIGS. 12 and 16 show the interaction between wire relief notch 112 and coring relief notch 88 at a position within the introducer 34 corresponding to firing device 124 being activated. Notably, the only portion of biopsy device 52 located at curve 42 upon activation of firing device 124 is flexible wall portion 118 of cannula 68 and flexible wall portion 120 of wire 76. Therefore, these two portions flex at the site of curve 42 and as a result little or no friction is registered at the curve during activation of the firing device 124. Moreover, since inner wall 46 of introducer 34 is slightly larger than the outer diameter $D_c$ of cannula 68, the introducer 34 provides support to flexible wall portions 118 and 120 of cannula 68 and wire 76, respectively.

FIGS. 8 and 13 best illustrate the sampling cavity 110. Wire relief notch 112 of wire 76 is arranged substantially symmetrical respective of reference axis Y. Flexible wall portion 120 of wire 76 is provided between approximately −135 and 135 degrees relative to the Y axis. Similarly, sampling cavity 110 is symmetrical relative to reference axis Y and therefore wire relief notch 112 and sampling cavity 110 are axially aligned.

Figure 15:
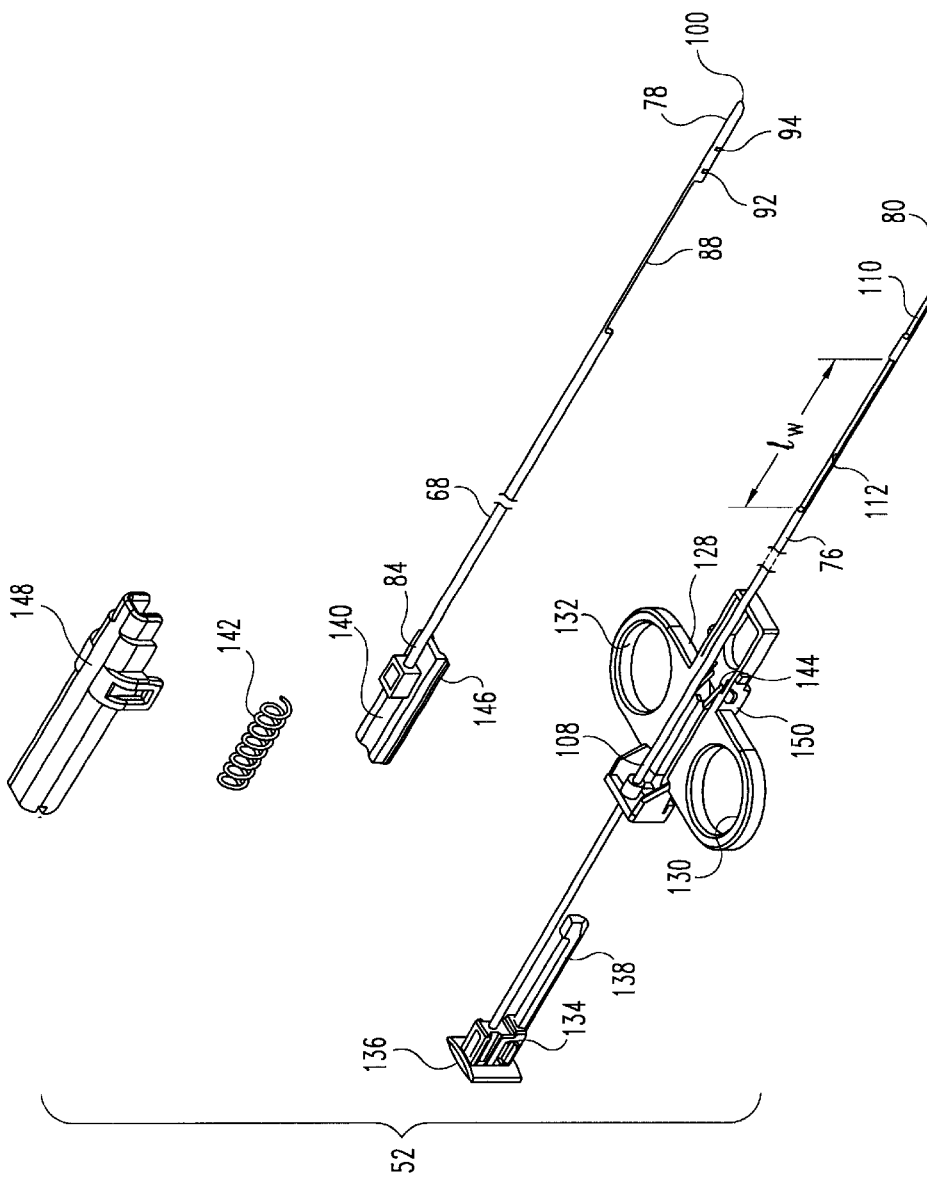
FIG. 15 is an exploded view of the biopsy assembly of FIG. 7.

Wire 76 is slidable relative to the coring cannula 68 between a first retracted position (FIG. 9) within the lumen 86 with the coring cannula 68 covering the sampling cavity 110 and a second, extended position (FIG. 8) wherein the distal end 80 of the wire 76 is extended away from the coring cannula 68 to expose the sampling cavity 110 to tissue at the biopsy site. A firing mechanism 124 is engaged to the proximal ends 84, 108 of the coring cannula 68 and the wire 76, respectively and is operable to move the coring cannula 68 relative to the wire 76 from the second position to the first position to trap tissue from the biopsy site in the sampling cavity 110. Any suitable firing mechanism is contemplated. In a preferred embodiment, the firing mechanism is a single action biopsy mechanism as shown in FIG. 15 and which is marketed by U.S. Biopsy, a division of Promex, Inc., Franklin, Ind.

Referring again to FIGS. 5 and 15, biopsy device 52 is provided with firing mechanism 124, which includes housing 128 having finger grips 130 and 132. An actuator 134 is operatively engaged to both the wire 76 and the coring cannula 68. The actuator 134 includes a gripping portion 136 and a drive mechanism 138. The drive mechanism 138 operates to depress a drive carriage 140 against the action of a spring 142. The housing 128 includes a resilient latch 144 that engages an underside 146 of the carriage 140 in the retracted position. The latch 144 is released by forward movement of the drive mechanism 138 so that the spring 142 pushes the carriage 140 outwardly which in turn thrusts cannula 76 over the sampling cavity 110 of the wire 76. Cover 148 snap-fits over housing 128 to protect spring 142 and the sliding engagement between carriage 140 and housing 128 from debris and interference. A suitable firing mechanism is disclosed in U.S. Pat. No. 6,056,760 filed Oct. 13, 1998. Firing mechanism 124 propels coring cannula 68 over wire 76 to trap tissue within sampling cavity 110 in wire 76. Although single action biopsy devices are effectively used to obtain tissue samples, double action firing devices, such as the device disclosed in U.S. Pat. No. 5,538,010 to Darr and Ireland may be used in place of the single action device.

In a preferred embodiment and as best seen in FIGS. 14 and 16, coring cannula 68 is fixed to drive carriage 140 such that discrete slots 92, 94 and coring relief notch 88 include their respective openings facing the underside 146 of drive carriage 140. Further, wire 76 is positioned on actuator 134 such that wire relief notch 112 is opposingly faced relative to underside 150 of firing mechanism housing 128. When firing mechanism 124 is assembled, wire relief notch 112 in wire 76 superposes coring relief notch 88 in coring cannula 68 and discrete slots 92, 94 in coring cannula 68 face underside 150 of firing mechanism housing 128.

Figure 18:
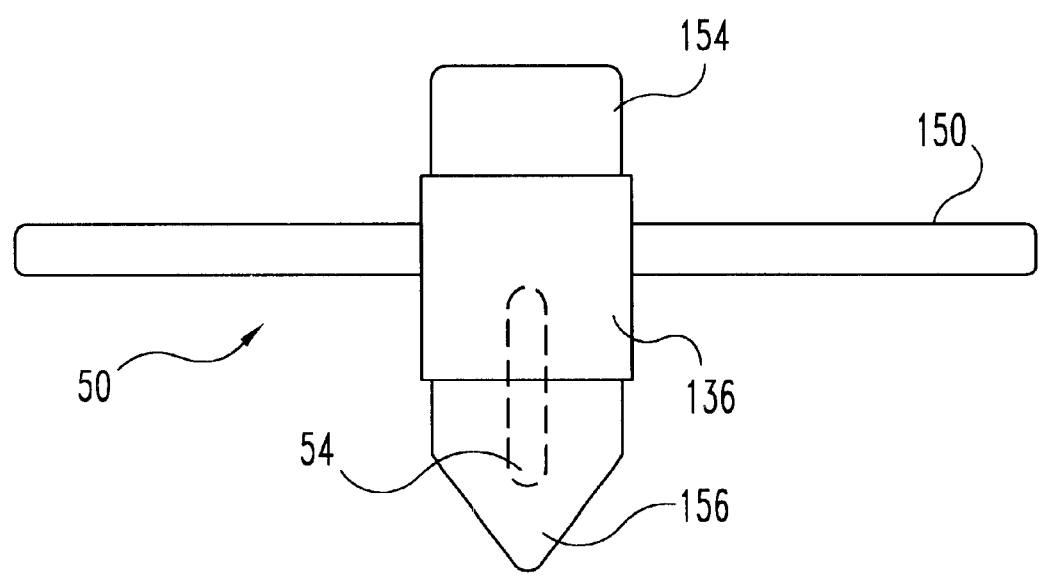
FIG. 18 is an end view of the biopsy device of FIG. 5, viewed along the line 18—18 of FIG. 5.

Coring cannula 68 and wire 76 traverse curve 42 in introducer 34, such that discrete slots 92, 94 in cannula 68 are axially aligned relative to inner radius 152 of curve 42. Inner radius 152 of curve 42 is located on reference axis Y (FIGS. 10–13). Flexible portions 96, 98 of cannula wall 82 provide the greatest degree of flexibility when discrete slots 92, 94 are circumferentially aligned with inner radius 152. Additionally, cannula 68 and wire 76 is most flexible traversing curve 42 in introducer when flexible wall portion 120 of wire 76, adjacently positioned relative to gap 122, overlays inner radius 152 of curve 42. To ensure cannula 68 and wire 76 is preferably inserted into introducer 34, flange 154 of introducer 34 preferably includes arrow-shaped portion 156 which aligns with underside 150 of firing mechanism 124 as shown FIG. 18.

In preparation for activating firing device 124, tip 38 of introducer 34 is ideally located in the hepatic vein and the cannula 68 and wire 76 are advanced into the proximal end 56 of the introducer 34. Preferably, underside 150 of firing mechanism 124 is circumferentially aligned with arrow shaped portion 156 of flange 154 and cannula 68 and wire 76 are advanced through introducer 34. Once underside 150 of firing mechanism 124 is aligned relative to arrow-shaped portion 156 of flange 154 and the cannula 68 and wire 76 are fully advanced within introducer 34, the firing mechanism 124 is poised for firing. Alternatively, similar results may be achieved if cannula and wire, 68, 76, are rotated 180° such that underside 150 of firing device 124 is circumferentially offset 180° relative to arrow shaped portion 156 of flange 154, as illustrated in FIG. 5. In this configuration discrete slots 92 and 94 in cannula 68 are circumferentially aligned with outer radius 158 of curve 42 in introducer 34. Consequently, as slots 92, 94 traverse curve 42 they tend to spread apart at outer surface 102 of cannula 68 rather than pinch together as illustrated in FIG. 14.

Figure 19:
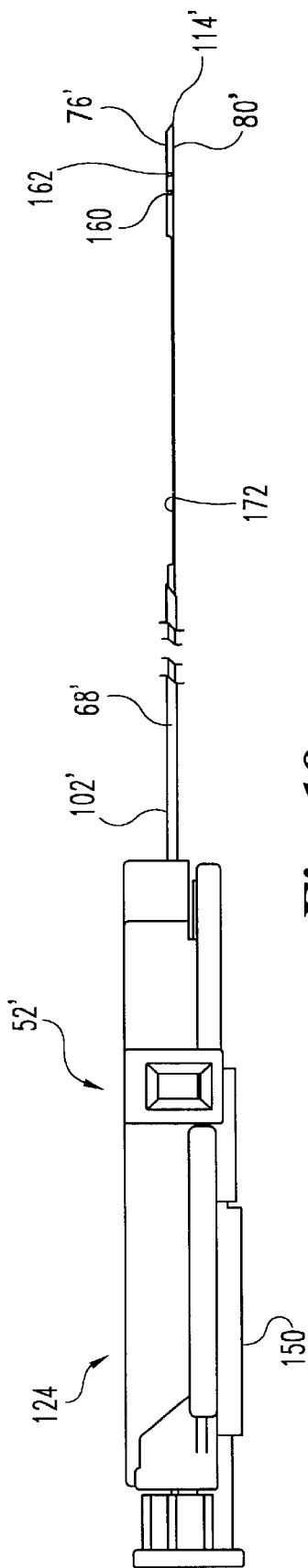
FIG. 19 is a plan view of a second embodiment of a biopsy device according to the present invention with the introducer removed.
Figure 20:
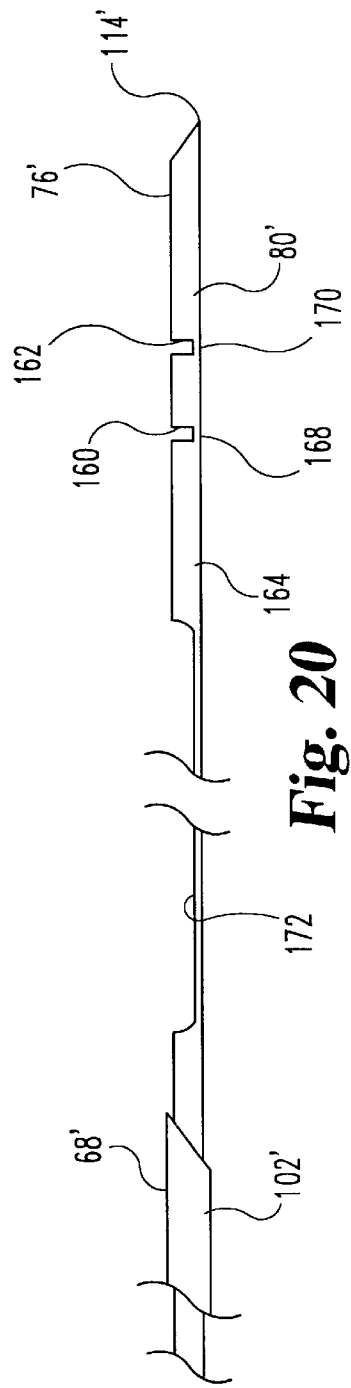
FIG. 20 is an enlarged fragmentary view of the biopsy device of FIG. 19, illustrating the distal end.

A second embodiment biopsy device according to the present invention is illustrated in FIGS. 19 and 20. Certain elements are indicated by primed reference numerals which indicate that the element has been modified relative to the corresponding element of the first embodiment. Biopsy device 52' includes cannula 68' and wire 76' operably engaged with firing device 124. In contrast to wire 76 of the first embodiment biopsy device 52 (FIGS. 7–9), wire 76' of second embodiment biopsy device 52' includes distal end 80' provided with a pair of discrete slots 160, 162. Each slot 160, 162 extends radially into surface 164 of wire 76', leaving respective semi-circular portions or flexing portions 168, 170 respectively positioned at the bottom of their respective slots. As tip 114' of wire 76' traverses curve 42 in introducer 34, each slot 160, 162 allows wire 76' to temporarily flex, significantly reducing sliding resistance between outer surface 102' of cannula 68' and inner surface 46 of introducer 34. Further, flexing portions 168, 170 are sized to allow flexibility in cannula 68' yet enough material is left such that permanent deformation of wire 76' is avoided. Each slot 160, 162 allows wire 76' to flex as it passes over outer radius 158 (FIGS. 12, 14 and 15) of curve 42 in introducer 34 to relieve resistance between cannula 68' and inside surface 46 of introducer 34 when cannula 68' and wire 76' are advanced toward flange 154 of introducer 34.

Wire 76' includes wire relief notch 172 which acts to decrease resistance between wire 76' and cannula 68' during firing of firing mechanism 124. Relief 172 also acts as a sampling cavity for liver tissue to be captured therein as wire 76' is advanced into the liver as previously described. Cannula 68', as illustrated in FIGS. 19 and 20, is a continuous cannula however it is envisioned that similar discrete slots (not shown), such as slots 92, 94 within cannula 68 of biopsy device 52 (FIGS. 8 and 9), may be provided in cannula 68' of biopsy device 52' to further decrease resistance at curve 42 of introducer 34.

In operation, the transvenous or transjugular liver biopsy procedure involves inserting the introducer cannula 34, which is a long, small diameter tube, into the internal jugular vein in the neck and is radiologically guided through a tortuous path of veins which lead to the liver, a distance of approximately 60 cm. Once the introducer 34 is positioned just outside of the liver, the cannula 68 and wire 76 are inserted through the lumen 36 and are then advanced directly into the liver to obtain a sample of tissue.

The introducer 34 is inserted into an incision made in the patient's jugular vein (FIG. 21) with the patient under local anesthetic. With the patient supine and positioned on a moveable table, the table is tilted a few degrees to distend the internal jugular and decrease the risk of air embolism.

Figure 21:
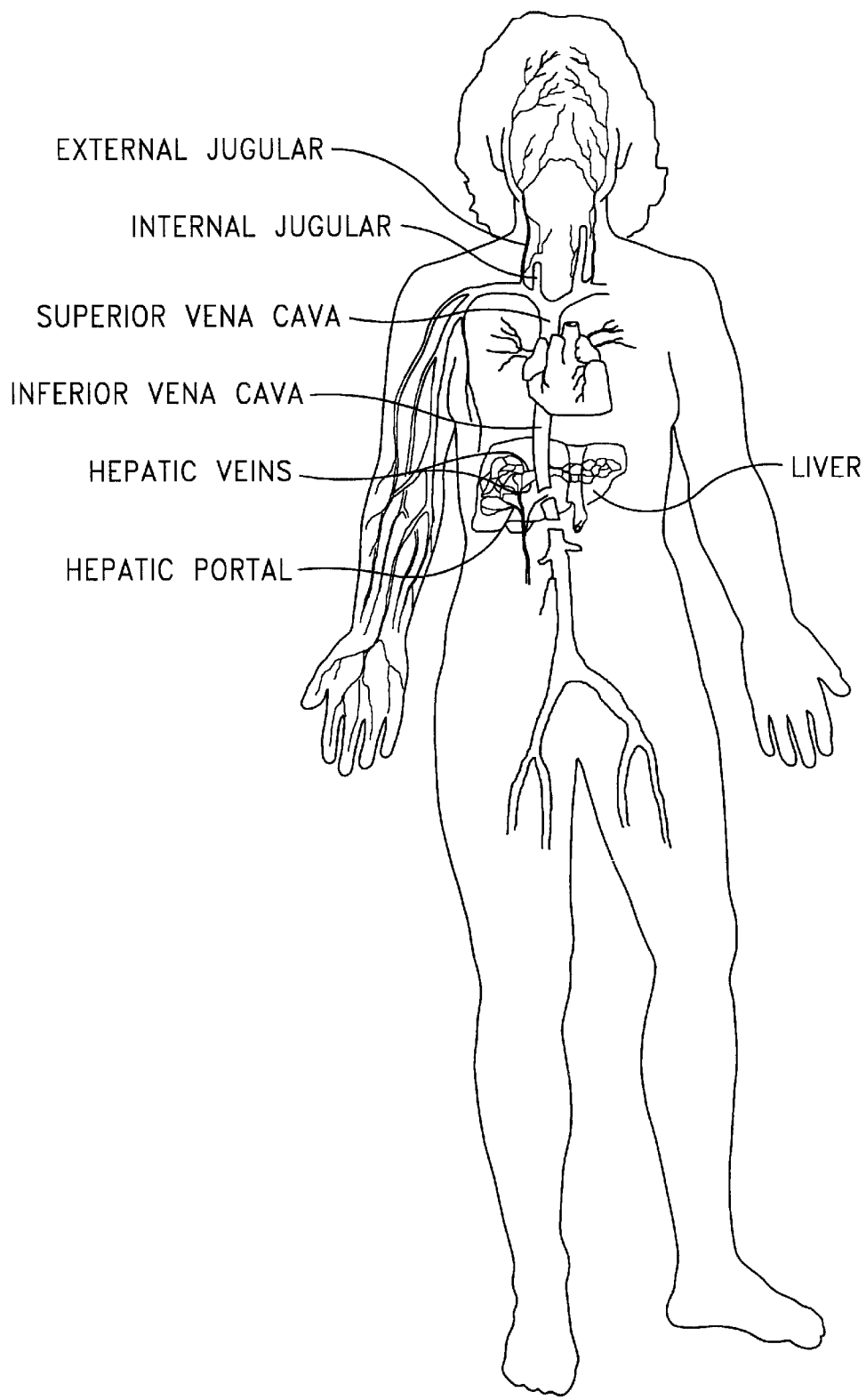
FIG. 21 is a diagrammatical view of the liver and venous system.

Referring to FIG. 21, the introducer is advanced along the inferior vena cava and into the right atrium. Positioning of the introducer is achieved through, for example, fluoroscopic X-ray or other imaging technique, as is customary. Tip 38 of introducer 34 includes a radio opaque marker (not shown) impregnated into a flexible outer sheath 75 to assist the surgeon in guiding the introducer to its target. Still within the inferior vena cava, the tip 38 of introducer 34 (FIG. 4) is carefully advanced through the inferior vena cava and positioned just above the level of the hepatic vein. The right or middle hepatic vein, if the introducer was placed in the patient's right jugular vein, for example, is then selected and the introducer tip 38 is advanced well into the liver through the hepatic vein. Occasionally, significant resistance is encountered when attempting to advance the introducer into the hepatic vein due to the confluence formed between the horizontally orientated hepatic vein and vertically oriented inferior vena cava. Introducer 34 includes the significant curve 42 located near its tip 38 to assist in traversing this confluence without significant difficulty.

During placement of the introducer, and once placement is achieved, further movement of the introducer is avoided to prevent damage to liver parenchyma, and in extreme instances, perforation of the liver capsule. Even slight movement of the introducer is avoided since the biopsy specimen is likely to be adversely affected if the introducer is dislodged from its ideal placement.

The present invention provides biopsy devices that are flexible yet self supporting for insertion into introducers. The flexible regions of the biopsy devices avoid binding and galling. This results in an improvement in the quality of the samples and durability of the devices. Moreover, the devices are not directional and they can be rotated within the introducer lumen to traverse curves within the introducer lumen. Although the devices of the present invention are remarkably flexible, the strength, durability and function of the assembly are not compromised.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy device having a flexible distal portion for obtaining a biopsy sample from a biopsy site, comprising:
   a coring cannula having a wall between a proximal end and a distal end and defining a lumen therebetween, said wall defining a coring relief notch adjacent said distal end, said coring relief notch having a length along a longitudinal axis of said cannula, said length of said coring relief notch longer than a width of said coring relief notch;
   a wire slidably disposed within said lumen of said coring cannula and having a proximal end and a distal end, said wire defining a sampling cavity adjacent said distal end and a wire relief notch adjacent said sampling cavity, said wire relief notch having a length along a longitudinal axis of said wire, said length of said wire relief notch longer than a width of said wire relief notch;
   said wire and said coring cannula having a first position with said wire retracted within said lumen so that said coring cannula covers said sampling cavity and a second position wherein said distal end of said wire is extended away from said coring cannula to expose said sampling cavity; and
   a firing mechanism engaged to said proximal ends of said coring cannula and said wire, said firing mechanism operable to move said coring cannula relative to said wire from the second position to the first position to trap tissue from the biopsy site in the sampling cavity.

2. The biopsy device of claim 1 wherein said wire relief notch is in communication with said coring relief notch when said wire and said coring cannula are in said first and second positions.

3. The biopsy device of claim 1 wherein said coring cannula further defines a slot adjacent said distal end.

4. The biopsy device of claim 3 wherein said slot is between said distal end and said coring relief notch.

5. The biopsy device of claim 3 wherein said coring relief notch is axially aligned with said slot.

6. The biopsy device of claim 3 wherein said sampling cavity is axially aligned with said wire relief notch.

7. The biopsy device of claim 3 wherein said coring cannula further defines a second slot adjacent said distal end.

8. A biopsy assembly, comprising:
   an introducer having
      an elongated cannula defining an introducer lumen defined between a proximal end and a distal end, said cannula having a curved portion adjacent said distal end;
      a body portion attached to said proximal end of said cannula and defining a channel in communication with said introducer lumen, and
      an access port defined in said body portion and in communication with said channel;
   a biopsy device disposed within said introducer lumen through said access port, said biopsy device including
      a coring cannula having a wall between a proximal end and a distal end and defining a lumen therebetween, said wall defining a coring relief notch adjacent said distal end, said coring relief notch having a length along a longitudinal axis of said coring cannula, said length of said coring relief notch longer than a width of said coring relief notch,
      a wire slidably disposed within said lumen of said coring cannula and having a proximal end and a distal end, said wire defining a sampling cavity adjacent said distal end and a wire relief notch adjacent said sampling cavity, said wire relief notch having a length along a longitudinal axis of said wire, said length of said wire relief notch longer than a width of said wire relief notch,
      said wire and said coring cannula having a first position with said wire retracted within said lumen so that said coring cannula covers said sampling cavity and a second position wherein said distal end of said wire is extended away from said coring cannula to expose said sampling cavity, and
      a firing mechanism engaged to said proximal ends of said coring cannula and said wire, said firing mechanism operable to move said coring cannula relative to said wire from the second position to the first position to trap tissue from the biopsy site in the sampling cavity; and
      said coring cannula and said wire being sufficiently flexible at said distal ends to traverse said curved portion as said biopsy device is inserted into said introducer lumen.

9. The biopsy assembly of claim 8 wherein said wire relief notch is in communication with said coring relief notch when said wire and said coring cannula are in said first and second positions.

10. The biopsy assembly of claim 8 wherein said coring cannula further defines a slot adjacent said distal end.

11. The biopsy assembly of claim 10 wherein said slot is between said distal end and said coring relief notch.

12. The biopsy assembly of claim 10 wherein said coring relief notch is axially aligned with said slot.

13. The biopsy assembly of claim 10 wherein said sampling cavity is axially aligned with said wire relief notch.

14. The biopsy assembly of claim 10 wherein said coring cannula further defines a second slot adjacent said distal end.

15. A biopsy device having a flexible portion for obtaining a biopsy sample from a biopsy site, comprising:

a coring cannula having a wall between a proximal end and a distal end and defining a lumen therebetween, said coring cannula defining a coring relief notch positioned at a location between said proximal end and said distal end, said coring relief notch having a length along a longitudinal axis of said cannula, said length of said coring relief notch longer than a width of said coring relief notch;

a wire slidably disposed within said lumen of said coring cannula and having a proximal end and a distal end, said wire defining a sampling cavity adjacent said distal end;

said wire and said coring cannula having a first position with said wire retracted within said lumen so that said coring cannula covers said sampling cavity and a second position wherein said distal end of said wire is extended away from said coring cannula to expose said sampling cavity;

a firing mechanism engaged to said proximal ends of said coring cannula and said wire, said firing mechanism operable to move said coring cannula relative to said wire from the second position to the first position to trap tissue from the biopsy site in the sampling cavity; and said wire further defining a wire relief notch at a location corresponding to said location of said coring cannula so that said wire relief notch is in communication with said coring cannula relief notch when said wire and said coring cannula are in said first and second positions.

* * * * *